United States Patent
Gabos et al.

(10) Patent No.: US 12,408,954 B2
(45) Date of Patent: Sep. 9, 2025

(54) SYSTEMS AND METHODS FOR EN BLOC DEROTATION OF A SPINAL COLUMN

(71) Applicant: Medos International Sarl, Le Locle (CH)

(72) Inventors: Peter Gabos, Glen Mills, PA (US); Thomas Runco, Providence, RI (US); Shawn Harris, Dighton, MA (US); Randal Betz, Jr., Wilmington, DE (US)

(73) Assignee: Medos International Sàrl, Le Locle (CH)

( * ) Notice: Subject to any disclaimer, the term of this patent is extended or adjusted under 35 U.S.C. 154(b) by 0 days.

(21) Appl. No.: 18/534,034

(22) Filed: Dec. 8, 2023

(65) Prior Publication Data
US 2024/0099747 A1    Mar. 28, 2024

Related U.S. Application Data

(63) Continuation of application No. 16/742,038, filed on Jan. 14, 2020, now Pat. No. 11,849,981.

(60) Provisional application No. 62/798,891, filed on Jan. 30, 2019.

(51) Int. Cl.
*A61B 17/70* (2006.01)
*A61B 17/56* (2006.01)

(52) U.S. Cl.
CPC ........ *A61B 17/708* (2013.01); *A61B 17/7077* (2013.01); *A61B 17/7079* (2013.01); *A61B 2017/564* (2013.01); *A61B 17/7047* (2013.01)

(58) Field of Classification Search
CPC ............ A61B 17/7077; A61B 17/7079; A61B 17/708; A61B 17/7076; A61B 17/7074
See application file for complete search history.

(56) References Cited

U.S. PATENT DOCUMENTS

| | | | |
|---|---|---|---|
| 7,179,261 B2 | 2/2007 | Sicvol et al. | |
| 7,670,358 B2 * | 3/2010 | Barry | A61B 17/7077 606/279 |
| 7,776,072 B2 | 8/2010 | Barry | |
| 7,951,175 B2 | 5/2011 | Chao et al. | |
| 8,361,121 B2 | 1/2013 | Barry | |
| 8,465,529 B2 | 6/2013 | Choi et al. | |
| 8,608,782 B1 * | 12/2013 | Rovner | A61B 17/7034 606/264 |
| 8,894,648 B2 * | 11/2014 | Dominik | A61B 17/7077 606/57 |
| 9,339,301 B2 | 5/2016 | Barry | |
| 9,339,308 B2 | 5/2016 | Mickiewicz et al. | |
| 9,668,787 B2 | 6/2017 | Barry | |
| 9,668,788 B2 | 6/2017 | Barry | |
| 9,949,764 B2 | 4/2018 | Di Lauro et al. | |
| 10,028,771 B2 | 7/2018 | Artaki et al. | |
| 10,098,665 B2 | 10/2018 | Rutschmann et al. | |
| 11,224,462 B2 | 1/2022 | Biedermann et al. | |
| 11,819,981 B2 | 11/2023 | Badeaux | |

(Continued)

*Primary Examiner* — Julianna N Harvey
(74) *Attorney, Agent, or Firm* — Barnes & Thornburg LLP

(57) ABSTRACT

Systems and methods for en bloc derotating a spinal column are provided. In one exemplary embodiment, the method can include manipulating first and second frames coupled respectively to a first set of vertebrae and a second set of vertebrae to derotate the first and second sets of vertebrae relative to one another, and subsequently locking a linkage assembly coupled respectively to the first and second frames to maintain the first and second sets of vertebrae in a derotated position.

12 Claims, 11 Drawing Sheets

(56) References Cited

U.S. PATENT DOCUMENTS

| | | | |
|---|---|---|---|
| 2006/0200132 A1* | 9/2006 | Chao | A61B 17/7077 606/279 |
| 2006/0201131 A1 | 9/2006 | McQuiggan et al. | |
| 2007/0213715 A1* | 9/2007 | Bridwell | A61B 17/025 606/264 |
| 2007/0213716 A1* | 9/2007 | Lenke | A61B 17/7032 606/264 |
| 2008/0294206 A1* | 11/2008 | Choi | A61B 17/7077 606/301 |
| 2011/0106082 A1* | 5/2011 | Kave | A61B 17/708 606/86 A |
| 2011/0172714 A1* | 7/2011 | Boachie-Adjei | A61B 17/7076 606/279 |
| 2012/0083853 A1* | 4/2012 | Boachie-Adjei | A61B 17/7014 606/86 A |
| 2012/0197297 A1* | 8/2012 | Bootwala | A61B 17/7077 606/246 |
| 2012/0203279 A1* | 8/2012 | Walters | A61B 17/7014 606/252 |
| 2013/0060294 A1 | 3/2013 | Donahue | |
| 2013/0211453 A1* | 8/2013 | Lenke | A61B 17/7077 606/250 |
| 2014/0039556 A1* | 2/2014 | Rutschmann | A61B 17/7002 606/266 |
| 2014/0046372 A1* | 2/2014 | Ibrahim | A61B 17/7049 606/279 |
| 2014/0277198 A1* | 9/2014 | Stad | A61B 17/7074 606/86 A |
| 2014/0316475 A1* | 10/2014 | Parikh | A61B 17/7086 606/86 A |
| 2016/0095634 A1* | 4/2016 | Meyer | A61B 17/7077 606/86 A |
| 2018/0014858 A1 | 1/2018 | Biester et al. | |
| 2018/0014862 A1 | 1/2018 | Raina et al. | |
| 2018/0049774 A1 | 2/2018 | Farmer et al. | |
| 2020/0237410 A1 | 7/2020 | Gabos et al. | |

* cited by examiner

SYSTEMS AND METHODS FOR EN BLOC DEROTATION OF A SPINAL COLUMN

CROSS-REFERENCE TO RELATED APPLICATIONS

This application is a continuation of U.S. application Ser. No. 16/742,038 filed on Jan. 14, 2020, and entitled "SYSTEMS AND METHODS FOR EN BLOC DEROTATION OF A SPINAL COLUMN," which claims priority to U.S. Provisional Patent Application No. 62/798,891 filed on Jan. 30, 2019, and entitled "SYSTEMS AND METHODS FOR EN BLOC DEROTATION OF A SPINAL COLUMN," the disclosures of which are incorporated herein by reference in their entireties.

FIELD

Systems and methods are provided for manipulating a spinal column.

BACKGROUND

Spinal deformities of varying etiologies which alter the natural alignment of the spine are well known. Such deformities include abnormal spinal curvatures such as scoliosis, kyphosis, and/or other abnormal curvatures. It is often necessary to surgically correct and stabilize spinal curvatures, which can be done through an open approach or through a minimally invasive approach. Surgical correction of complex spinal deformities can involve manipulating vertebrae in sagittal, coronal, and/or transverse planes. Transverse plane rotation of a vertebra, e.g., about a rotation axis that extends generally in a superior-inferior direction, towards a more natural anatomical alignment is often referred to as derotation.

Derotation and other surgical correction typically includes the repositioning and realignment of one or more vertebra in the spinal column. However, such repositioning and realignment can be time-consuming, cumbersome, and potentially difficult to achieve during a surgical procedure. For example, the alignment of multiple vertebral levels can require manipulation of instrumentation that calls for additional assistance to help the surgeon maintain intermediate and final derotation of the spinal column while additional correction maneuvers (e.g., compression, distraction, and the like) and tightening of set screws are performed during the surgical procedure. Further, forces applied to the one or more vertebra need to be controlled to minimize stresses on the spinal column and implants (e.g., spinal rods, bone anchors, set screws, etc.).

Accordingly, there is a need for improved systems and methods for surgically correcting and stabilizing spinal curvatures.

SUMMARY

Exemplary methods for en bloc derotation of a spinal column are provided. In one embodiment, the method includes coupling a first clamp to a first screw extension coupled to a first vertebra, coupling a second clamp to a second screw extension coupled to a second vertebra, rotating the first and second clamps relative to one another to derotate the first vertebra and the second vertebra relative to one another, and coupling a linkage to the first and second clamps and locking the linkage to maintain the first and second clamps in a fixed position relative to one another, thereby maintaining the first vertebra and the second vertebra in a derotated position relative to one another. In one embodiment, the first vertebra can be located in the lumbar spine and the second vertebra can be located in the thoracic spine.

In some embodiments, coupling the first clamp to the first screw extension coupled to the first vertebra can further include coupling the first clamp to a third screw extension coupled to a third vertebra, and coupling the second clamp to the second screw extension coupled to the second vertebra can further include coupling the second clamp to a fourth screw extension coupled to a fourth vertebra.

The linkage can be locked in a variety of ways. For example, in some embodiments, locking the linkage can include rotating a locking element on the linkage to lock first and second arms of the linkage in a fixed angular orientation relative to one another. Further, the linkage can be coupled to the first screw to the first screw extension in a variety ways. For example, in some embodiments, coupling the linkage to the first and second clamps can include inserting a first connector at a first end of the linkage into a first receiving member of the first clamp, and inserting a second connector at a second end of the linkage into a second receiving member of the second clamp. The first and second connectors can each include a pair of legs and the first and second receiving members can each include a pair of bores that receives the legs when the first and second connectors are coupled to the first and second receiving members.

In some embodiments, the method can also include, prior to coupling the first and second clamps, driving a first bone anchor into the first vertebra to couple the first screw extension to the first vertebra, and driving a second bone anchor into the second vertebra to couple the second screw extension to the second vertebra. In some embodiments, the method can also include coupling the linkage to a support member mounted on an operating table.

In another embodiment, the method can include manipulating first and second clamps coupled respectively to a first plurality of vertebrae and a second plurality of vertebrae to derotate the first and second plurality of vertebrae relative to one another, and subsequently locking first and second arms of a linkage assembly coupled respectively to the first and second clamps to maintain the first and second arms in a first angular orientation relative to one another, thereby maintaining the clamps in a fixed position and maintaining the first and second plurality of vertebrae in a derotated position. In one embodiment, the first plurality of vertebrae can be located in the lumbar spine and the second plurality of vertebrae can be located in the thoracic spine.

In some embodiments, the method can also include, prior to locking, non-rotatably coupling the first arm of the linkage assembly to the first clamp and non-rotatably coupling the second arm of the second linkage assembly to the second clamp. In other embodiments, the method can also include coupling the linkage to a support member mounted on an operating table.

The linkage can be locked in a variety of ways. For example, in some embodiments, locking the linkage can include rotating a locking element on the linkage.

In another embodiment, the method can include clamping a first frame to a first plurality of fixture elements coupled to a first plurality of vertebrae, clamping a second frame to a second plurality of fixture elements coupled to a second plurality of vertebrae that differs from the first plurality of vertebrae, rotating the first plurality of fixture elements and the second plurality of fixture elements relative to each other, thereby manipulating at least a portion of the spinal column into a derotated configuration, attaching a first end of a first arm of a linkage assembly to the first frame and a second end of a second arm of the linkage assembly to the second frame so as to bridge the first plurality of fixing elements to the second plurality of fixing elements, and locking the first and second arms of the linkage assembly relative to one another to lock the first plurality of fixture elements and the second plurality of fixing elements in a fixed position relative to each other such that the spinal column is maintained in the derotated configuration. In one embodiment, the first plurality of vertebrae can be located in the lumbar spine and the second plurality of vertebrae can be located in the thoracic spine.

In some embodiments, attaching the first end of the first arm to the first frame can include inserting first and second male members into first and second receivers in the first frame, and attaching the second end of the second arm to the second frame can include inserting third and fourth male members into third and fourth second receivers in the second frame.

The method can also include additional steps. For example, in one embodiment, the method can also include coupling the linkage assembly to a support member mounted on an operating table. In some embodiments, the method can also include applying a compression force to first and second fixture elements of the first plurality of fixture elements to cause respective vertebra coupled thereto to move towards each other. In other embodiments, the method can also include applying a distraction force to first and second fixture elements of the first plurality of fixture elements to cause respective vertebra coupled thereto to move away from each other. In yet other embodiments, the method can also include prior to clamping the first and second frames, driving a bone anchor coupled to each of the first and second plurality of fixture elements into the first and second plurality of vertebrae to couple the first and second plurality of fixture elements to the first and second plurality of vertebrae.

BRIEF DESCRIPTION OF THE DRAWINGS

This invention will be more fully understood from the following detailed description taken in conjunction with the accompanying drawings, in which.

DETAILED DESCRIPTION

Figure 1:
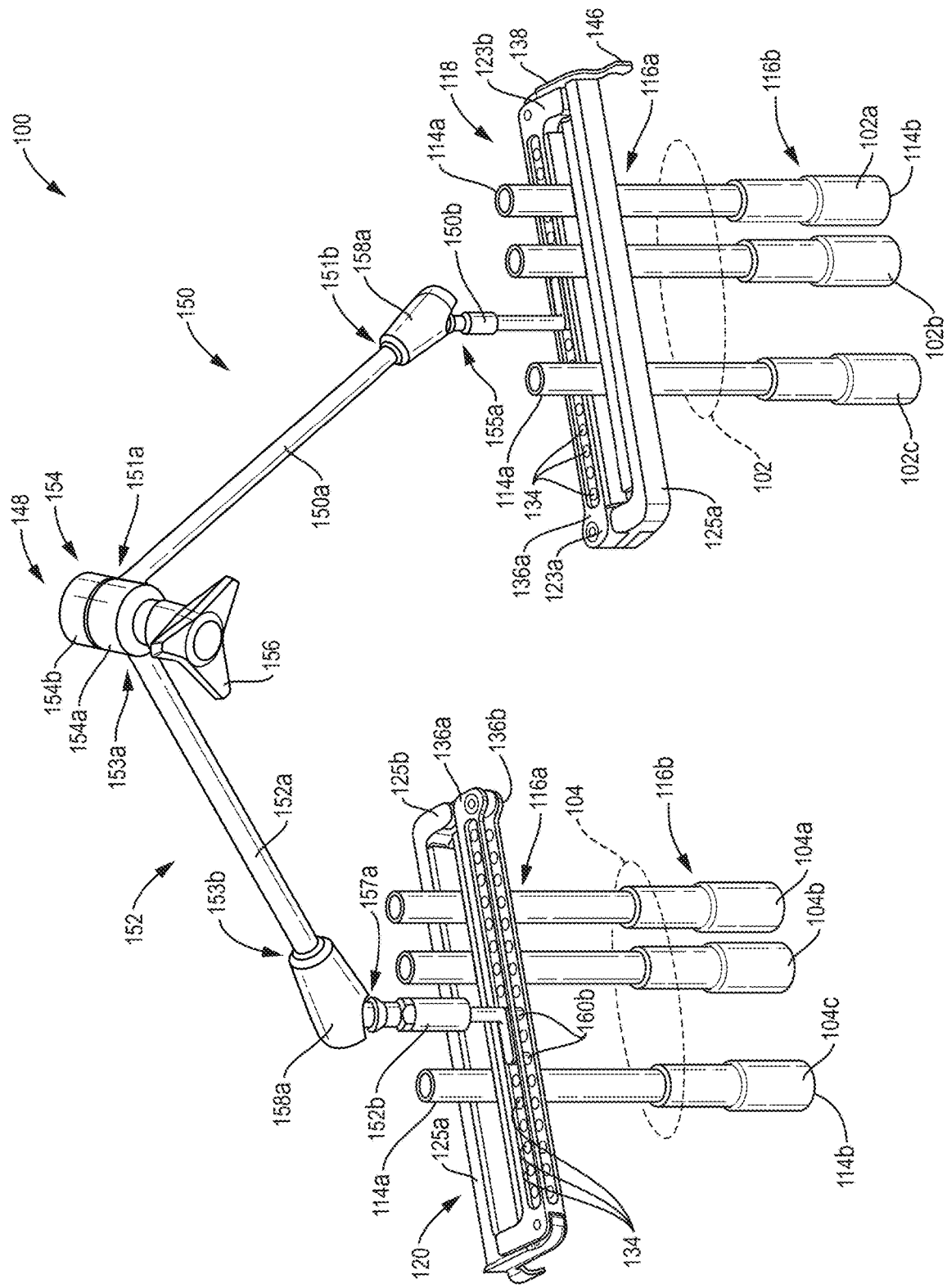
FIG. 1 is a perspective view of a system that includes a first set of fixing elements clamped together by a first frame, a second set of fixing elements clamped together by a second frame, and a linkage having first and second linking arms coupled respectively to the first and second frames.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Systems and methods for en bloc derotation of a spinal column are provided. These systems and methods allow for en bloc derotation of multiple vertebra and the stabilization of derotated vertebra while additional correction maneuvers are being performed (e.g., compression, distraction, contouring, and the like). The stabilization of derotated vertebra can allow for controlled final tightening across multiple fixation points along the spinal column. As a result, such stabilization can restore corrective maneuvers and final tightening back to the hands of the surgeon, with less reliance on other assistants (e.g., another surgeon or nurse). Thus, the present systems and methods can reduce the complexity of spinal deformity correction procedures, minimize the risk of further inadvertent rotation/derotation of the derotated vertebra while subsequent surgical procedures are being performed on the spinal column, and reduce the risk of damage to implants and the vertebral bodies due to high stress concentration at the implant-vertebra interface.

An en bloc derotation method typically includes inserting bone anchors into a plurality of vertebrae, coupling fixing elements to at least a portion of the bone anchors, clamping a first portion of fixing elements together, clamping a second portion of fixing elements together, and rotating the first and second portions relative to each other so as to derotate at least a portion of the spinal column. Clamping or otherwise connecting or joining multiple fixing elements together can allow the vertebrae to which the fixing elements are coupled to be derotated or manipulated as a group, e.g., simultaneously or in unison. For example, in some embodiments, a first set of bone anchors can be inserted into a first set of vertebrae and a second set of bone anchors can be inserted into a second set vertebra along a spinal column. In certain embodiments, the first set of vertebrae can be located in the lumbar spine and the second set of vertebrae can be located in the thoracic spine. The bone anchors can be positioned on opposite lateral sides of the spinal column (e.g., a concave side and a convex side of a scoliotic curve). Once the bone anchors are inserted, a first spinal rod is inserted into a receiving member of the bone anchors located on a first side of the spinal column (e.g., the concave side). Additionally, a second spinal rod can be inserted into a receiving member of the bone anchors located on a second side of the spinal column (e.g., the convex side). Before or after the first spinal rod is seated within the bone anchors, fixing elements are coupled to at least a portion of the bone anchors in the first and second sets of vertebrae. The fixing elements coupled to bone anchors on the first side (first segment of fixing elements) can be clamped together (e.g., by a first frame or clamp) and the fixing elements coupled to bone anchors on the second side (second segment of fixing elements) can be clamped together (e.g., by a second frame or clamp). The first and second segments of fixing elements can be rotated relative to each other to derotate the vertebrae connected thereto. Once in a derotated position, the surgeon can perform additional correction maneuvers and/or tightening of the bone anchors to an attached spinal rod. However, maintaining the derotated position during this time can be difficult. For example, an assistant (e.g., an additional surgeon) is typically needed to manually hold the first and second segments of fixing elements in place. As a result, multiple skilled users are required and tactile feedback or operative "feel" to each user can be reduced.

In general, systems and methods described herein use at least two fixing elements (e.g., screw extensions) that can be coupled to different vertebra of a spinal column, and first and second frames that can be coupled to different fixing element(s) of the at least two fixing elements. As a result, the first and second frames allow a surgeon to derotate different portions of the spinal column relative to each other and/or at the same time. The system also includes a linkage that can selectively couple to and lock the first and second frames so as to maintain the first and second frames in a fixed position relative to one another, e.g., after manipulation of the vertebrae into a derotated position. As described in more detail below, the linkage therefore functions as a stabilization mechanism that maintains the different vertebrae in the derotated position, thereby allowing the surgeon to perform further correction maneuvers (e.g., compression, distraction, contouring) on the spinal column and/or to secure implants, such as spinal rods, to the spinal column. As used herein, the term "frame" is used synonymously with the term "clamp," and the term "linkage" is used synonymously with the term "linkage assembly."

FIG. 1 illustrates an exemplary embodiment of a system 100 for use in an en bloc derotation method. As shown, the system 100 includes a first set of fixing elements 102, a second set of fixing elements 104, first and second frames 118, 120, and a linkage 148. Each of these components will be described below in connection with the method for en bloc derotation of a spinal column, shown in FIGS. 2-3 and 5-6. While the system 100 can be used to derotate various curve patterns of a spinal column, the method in FIGS. 2-5 illustrates derotation of a spinal column 101 having a right thoracic curve pattern. As a result, the spinal column 101 has a concave side (A) and a convex side (B).

Figure 2:
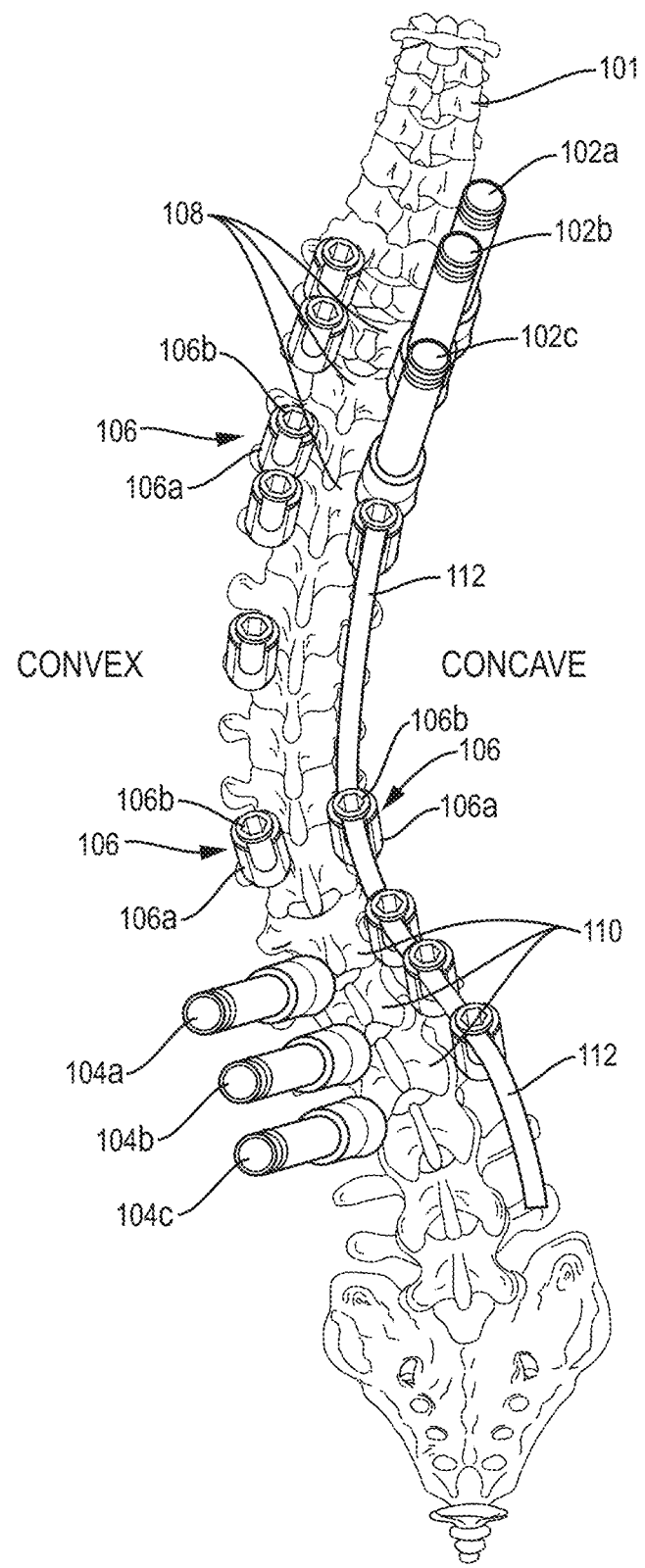
FIG. 2 is a perspective view of the first set of fixing elements and the second set of fixing elements of FIG. 1 shown coupled to a spinal column.

In FIG. 2, bone anchors 106 are implanted in multiple vertebrae along the spinal column 101. In this illustrated embodiment, the first set of fixing elements 102 are coupled to respective bone anchors implanted in a first set of vertebrae 108 extending along a first position of the spinal column 101, and the second set of fixing elements 104 are coupled to respective bone anchors implanted into a second set of vertebrae 110 extending along a second portion of the spinal column 101. While the first and second sets of fixing elements 102, 104 can be coupled to bone anchors located along any portion of the spinal column, in some embodiments, as shown in FIG. 2, the first set of fixing elements 102 are located in the thoracic spine and the second set of fixing elements 104 are located in the lumbar spine.

As shown, the first and second sets of vertebrae 108, 110 differ from one another, and each fixing element of the first and second set of fixing elements 102, 104 are coupled to a different vertebra. While the number of fixing elements can vary depending at least on the curve pattern of the spinal column, the illustrated first and second sets of fixing elements 102, 104 each include three separate fixing elements 102a, 102b, 102c, 104a, 104b, 104c.

The bone anchors 106 inserted along the spinal column 101 can be substantially similar in structural configuration. Each bone anchor 106 has a receiving member 106a configured to receive a spinal fixation element, e.g., a spinal rod, a screw having an elongate threaded shaft (not shown) extending from the receiving member 106a, and a securing element 106b, such as a set screw or other locking mechanism. As shown in FIG. 2, each receiving member 106a is in the form of a u-shaped head that seats the rod and each securing element 106b is a set screw with external threads that engage the grooves of the head. As will be appreciated by a person skilled in the art, any bone anchor, configured to engage bone and seat and secure a spinal fixation element can be used in a surgical system including any of the surgical systems described herein. Exemplary embodiments of bone anchors are described in more detail in U.S. Patent Publication Nos. 2006/0200131, 2006/0200132, 2013/0060294, 2018/0014858, 2018/0014862 and U.S. Pat. No. 7,179,261, each of which is hereby incorporated by reference in its entirety. It should be noted that the number and placement of the bone anchors depend at least on the curve pattern of the spinal column and therefore are not limited to the number and placement illustrated in the figures.

Further, prior to or after coupling the first and second plurality of fixing elements 102, 104 to respective bone anchors, as shown in FIG. 2, a first spinal rod 112 can be inserted through the receiving members 106a of the bone anchors 106 along at least a portion of the concave side of the spinal column 101. As discussed in more detail below, once the spinal column 101 is in a desired derotated configuration, the securing elements 106b can be tightened, thereby securing the first spinal rod 112 to respective bone anchors 106. In some embodiments, prior to or after coupling the first and second sets of fixing elements 102, 104, a second spinal rod (not shown) can also be inserted through the receiving members 106a of bone anchors positioned along at least a portion of the convex side of the spinal column 101.

The first and second sets of fixing elements 102, 104 can have a variety of configurations. As shown, each fixing element 102a, 102b, 102c, 104a, 104b, 104c is in the form of a screw extension having an elongated, cylindrical shape that extends from a first end 114a to a second end 114b. As shown, the second end 114b of each fixing element is releasably engaged to a respective bone anchor. In other embodiments, the fixing elements 102a, 102b, 102c, 104a, 104b, 104c can be integral with the bone anchors.

The fixing elements 102a, 102b, 102c, 104a, 104b, 104c each have a substantially constant outer diameter along a first end portion 116a thereof and an enlarged outer diameter along a second end portion 116b thereof. In other embodiments, one or more fixing elements can have a substantially constant outer diameter along its length extending from its first end to its second end. As will be appreciated by a person skilled in the art, the fixing elements can have any size, shape, and configuration, same or different from one another. Exemplary embodiments of fixing elements are described in more detail in U.S. Patent Publication No. 2006/0200132 and U.S. Pat. Nos. 7,179,261 and 9,339,308, each of which is hereby incorporated by reference in its entirety.

Figure 3:
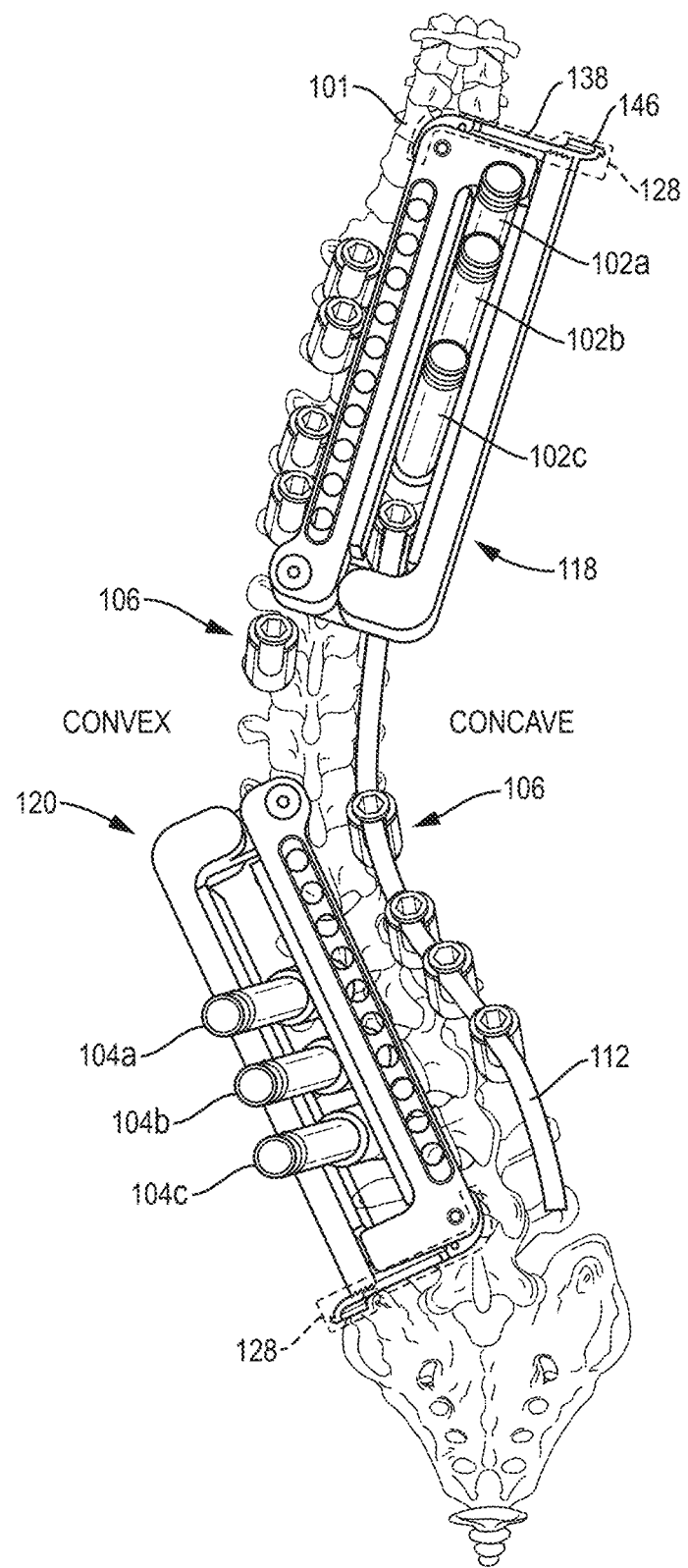
FIG. 3 is a perspective view of the first set of fixing elements and the second set of fixing elements of FIG. 2 clamped together by first and second frames, respectively, prior to derotation of the spinal column.

With the fixing elements coupled to their respective vertebra, the first set of fixing elements 102 can be clamped together using a first frame 118 and the second set of fixing elements 104 can be clamped together using a second frame 120, as shown in FIG. 3. As a result, the first set of fixing elements 102 are clamped separate and apart from the second set of fixing elements 104, and vice versa.

As shown in FIG. 3, the first and second frames 118, 120 each include two arm members 122, 124 that extend from a first end 122a, 124a to second end 122b, 124b, a first pivot pin 126, and a locking mechanism 128. For sake of simplicity, the following description is with respect to the first frame 118. A person skilled in the art will understand, however, that the following discussion is also applicable to the second frame 120, which as shown in FIG. 3 is structurally similar to that of the first frame 118. The first frame 118 is illustrated in more detail in FIGS. 4A-4C As shown in FIGS. 1 and 3-4C, the two arm members 122, 124 are pivotally coupled together at their first ends 122a, 124a via the first pivot pin 126 such that each arm member 122, 124 can move relative to each other. As a result, the first pivot pin 126 attaches the two arm members 122, 124 in a manner that allows the first frame 118 to move between open and closed positions. Once the first frame 118 is in the open position, the first end portions 116a of the first set of fixing elements 102 can be placed between the two arms members 122, 124 of the first frame 118. The two arm members 122, 124 can then be closed to form a rectangular slot 130 within which the first set of fixing elements are held, as shown in FIG. 3. It should be noted that the slot can have a variety of shapes and sizes.

The two arm members 122, 124 can have a variety of configurations. As shown, each arm member 122, 124 includes two segments 123a, 123b, 125a, 125b that extend at about 90 degrees relative to each other. As such, in this illustrated embodiment each arm member 122, 124 has a substantially L-shaped configuration. While the two segments 123a, 123b, 125a, 125b can have a variety of lengths relative to each other, the first segments 123a, 125a as shown in FIGS. 1 and 3-4C, each have a length that is greater than a length of the second segments 123b, 125b. Further, the first segments 123a, 125a each include a pad 132 that is configured to help secure, and therefore restrict motion between, the first set of fixing elements 102 when clamped within the first frame 118. As shown in FIGS. 1 and 3-4C, the pads 132 are positioned along opposing internal surfaces of the first segments 123a, 125a so that the pads abut against the first set of fixing elements 102 when the first frame 118 is in the closed position. The pads 132 can be formed from a compressible and/or resilient material such as silicone to allow the pads 132 to deform around the first set of fixing elements 102 when the frame 118 is clamped thereto. The pads 132 can have material properties or surface configurations to provide increased friction and a stronger grip on the first set of fixing elements 102 when clamped by the frame 118. It will be appreciated that the geometries of the frame 118 and the first set of fixing elements 102 can allow the frame to be clamped at any of a plurality of locations along the length of the fixing elements, and can allow the frame to be clamped to a plurality of fixing elements, contacting each fixing element at a different point along the length of the fixing element. This can allow attachment of the frame 118 to the first set of fixing elements 102 without changing sagittal alignment of the attached vertebrae.

Further, as shown in FIGS. 1 and 3-4C, the first segment 123a of the first arm member 122 includes a set of mating features 134 defined along at least a portion of its length (L). Each mating feature is configured to receive a connector (e.g., a male connector), like connector 160 in FIG. 6, as discussed in more detail below. As such, the shape and size of the mating features 134 depend at least in part on the shape and size of the connector(s). While the mating features 134 can have a variety of configurations, the mating features 134 as shown are in the form of bores. In this illustrated embodiment, each bore has a substantially circular cross-section and extends from a first surface 136a to a second, opposing surface 136b of the first segment 123a. In other embodiments, one or more bores can extend partially through the first segment 123a. Further, in some embodiments, the size and/or shape of the mating features 134 can vary relative to each other. It should be noted that other mating features can be used.

Figure 4B:
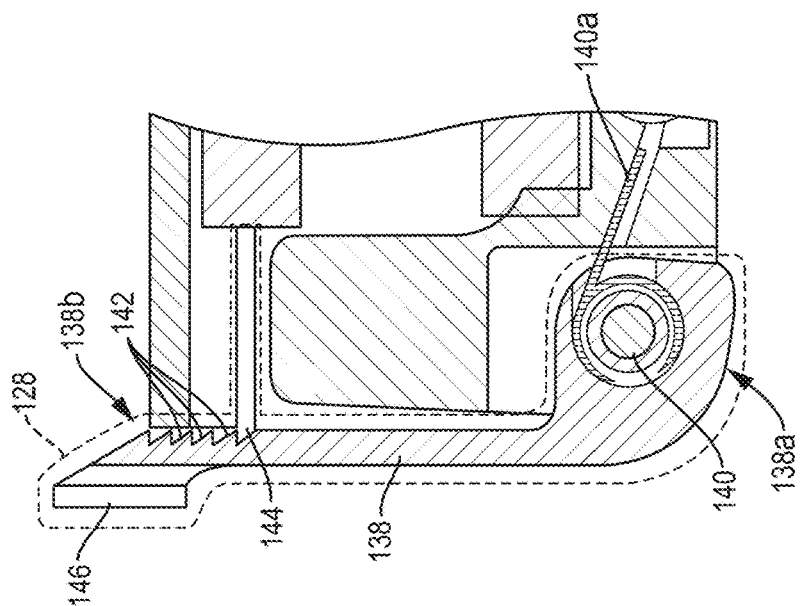
FIG. 4B is a cross-sectional view of the first frame of FIG. 4A taken at line 4B-4B.
Figure 4A:
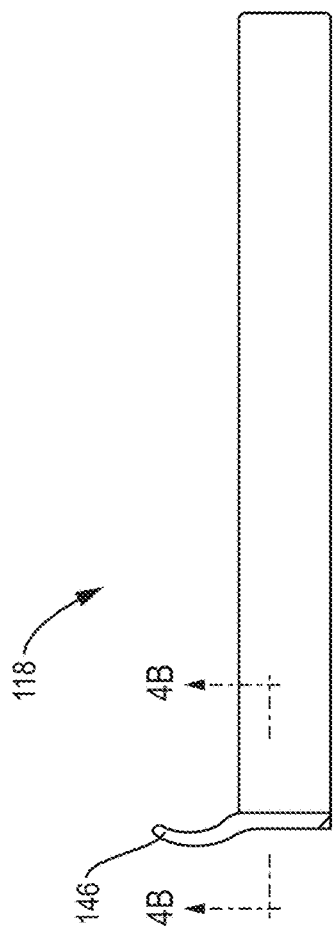
FIG. 4A is a side view of the first frame in FIG. 3.
Figure 4C:
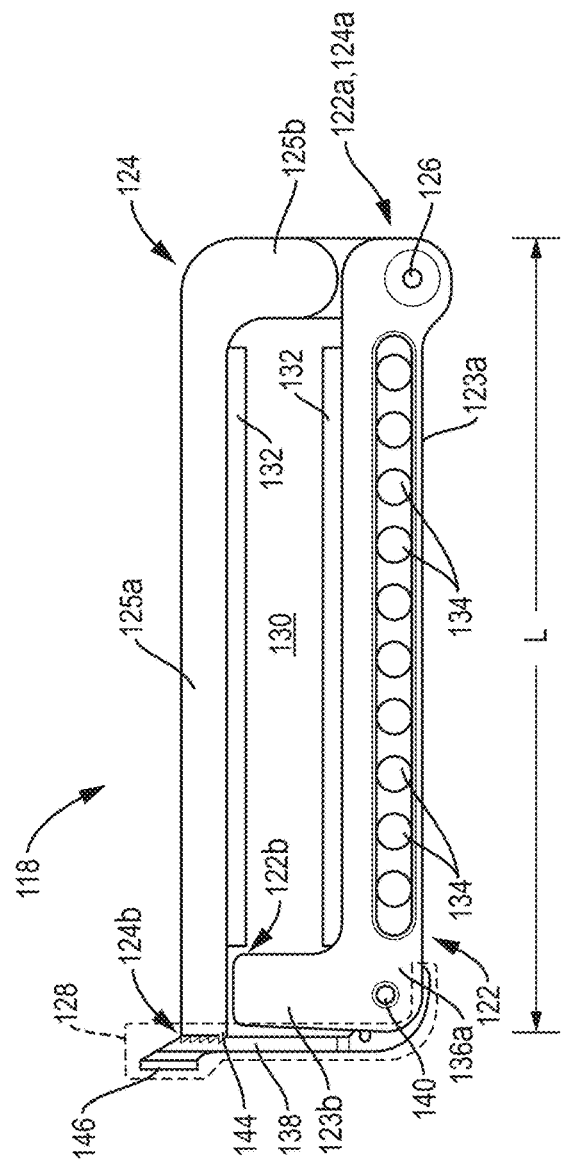
FIG. 4C is a top view of the first frame of FIG. 3.

The first frame 118 also includes a locking mechanism 128 that is configured to selectively lock the two arm members 122, 124 together when the first frame 118 is closed. The locking mechanism 128 can have a variety of configurations. For example, as shown in FIGS. 4A-4C, the locking mechanism 128 includes a locking arm 138 having a first end 138a that is pivotally coupled to the first arm member 122 at a second pivot pin 140 engaged with a torsion spring 140a, and a second end 138b that is configured to engage with the second arm member 124 as the first frame 118 is moved into a closed position. The second end 138b of the locking arm can include a plurality of teeth 142 extending from an inner surface thereof that is configured to receive a pawl element 144 that extends from the second end 124b of the second arm member 124. As a result, when the first frame 118 moves to a closed position to clamp the first set of fixing elements 102 together, as shown in FIG. 3, the pawl element 144 ultimately engages with and translates along the set of teeth 142 in a direction towards the first arm member 122. Thus, the two arms members 122, 124 are selectively locked together by ratcheting.

The locking arm 138 is also designed to disengage with the second arm member 124 of the first frame 118. As shown in FIGS. 1 and 4A-4C, the locking arm 138 also includes a release element 146 that is configured to disengage the pawl element 144 from the set of teeth 142 to unlock the first frame 118. The release element 146 can have a variety of configurations. For example, as shown in FIGS. 1 and 3-4C, the release element 146 is a lever that extends outward from the second end 138b of the locking arm 138. In use, a user (e.g., the surgeon) applies a force to the lever to cause the locking arm 138 to pivot away from the first frame 118. As a result, the pawl element 144 slides out of engagement with the plurality of teeth 142, and thus the locking arm 138, thereby unlocking the first frame 118. Once the first frame 118 is unlocked, the first and second arm members 122, 124 are able to move freely relative to each other.

Figure 5:
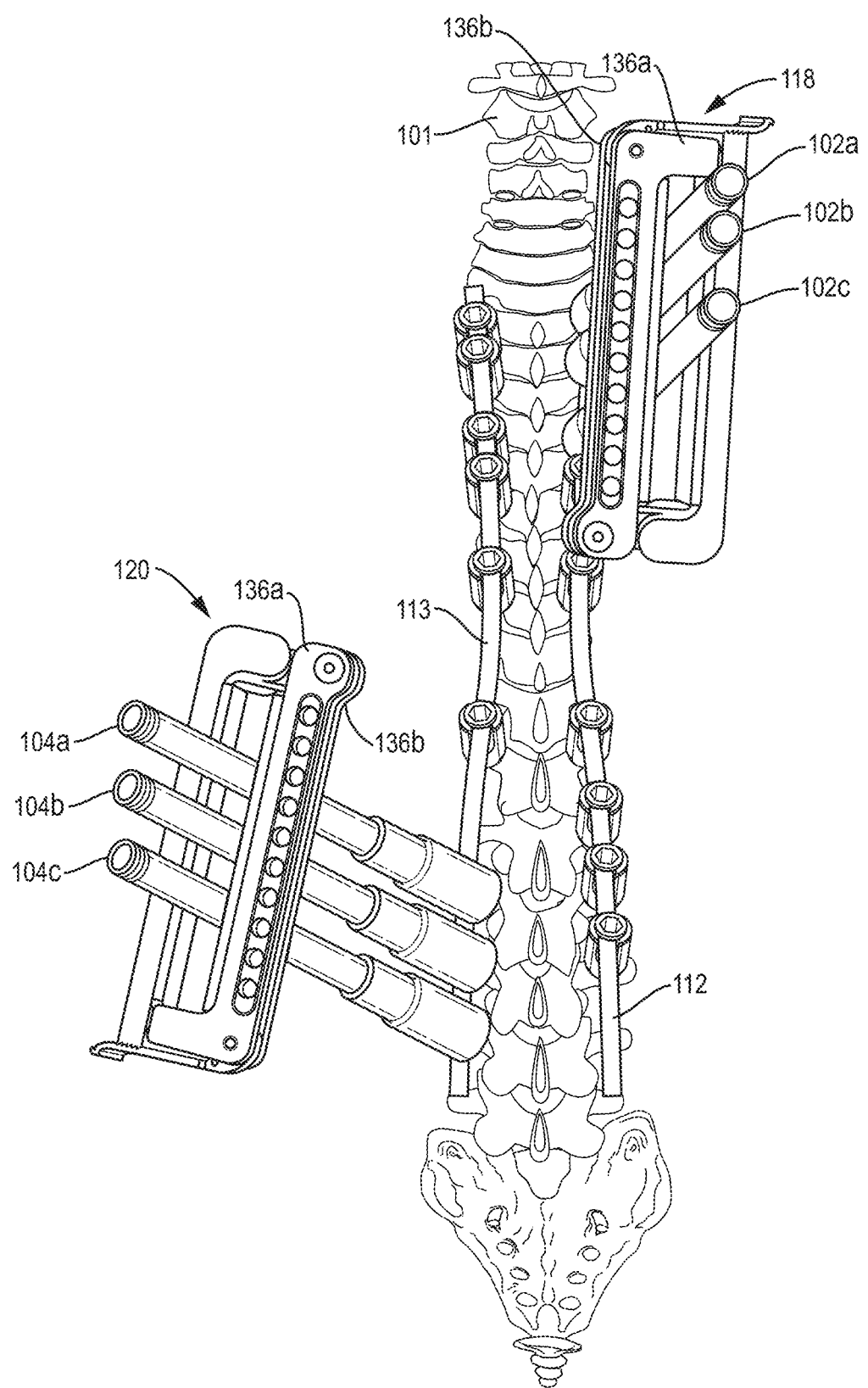
FIG. 5 is a perspective view of the first and second set of fixing elements and the first and second frames of FIG. 3, shown after derotation of the spinal column.
Figure 6:
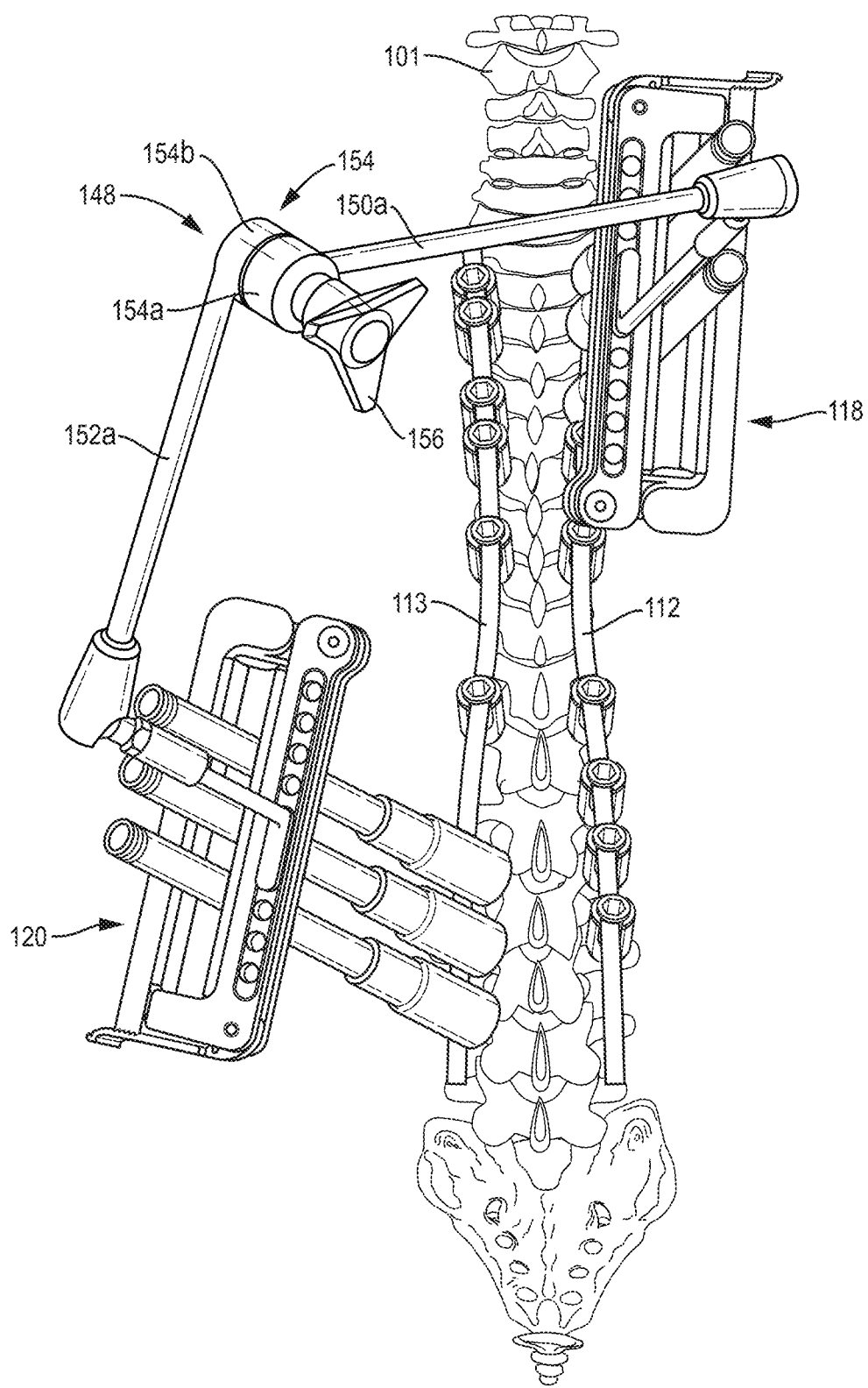
FIG. 6 is a perspective view of the first and second frames of FIG. 4 shown coupled together by the linkage of FIG. 1, after derotation of the spinal column.

After the first and second sets of fixing elements 102, 104 are clamped together using the first and second frames 118, 120, the surgeon moves the first and second frames 118, 120 relative to each other to manipulate at least a portion of the spinal column 101, as shown in FIG. 5. For example, en bloc derotation can be achieved by causing the first frame 118 to revolve around or orbit superior-inferior axes of the vertebrae to which it is coupled, thereby rotating said vertebrae in respective transverse planes. During this movement of the first frame 118, the second frame 120 can be maintained in a fixed location, or can likewise be manipulated to revolve around or orbit superior-inferior axes of the vertebrae to which it is coupled, thereby rotating said vertebrae in respective transverse planes. The first and second frames 118, 120 can be moved in opposite directions, e.g., such that they move generally towards or away from one another and such that the groups of vertebrae to which they are coupled rotate relative to one another. In this illustrated embodiment, the first and second frames 118, 120 are moved away from each other to thereby rotate the vertebrae back into transverse plane alignment. As also shown in FIG. 5, correction of the spinal column 101 in the sagittal and coronal planes can be performed using known techniques, before, during, or after applying axial derotation. Once the spinal column 101 is in a derotated configuration, the linkage 148 can be coupled to the first and second frames 118, 120 and locked, as shown in FIG. 6. Once locked, the linkage 148 maintains the derotated configuration without requiring user assistance. It should be noted that the linkage 148 can also be provisionally locked during incremental rotations of the first and second frames 118, 120.

With the linkage 148 locked, a second spinal rod 113 can be inserted through the receiving members 106a of the bone anchors 106 positioned along at least a portion of the spinal column 101. Alternatively, as noted above, the second spinal rod 113 can be inserted prior to coupling the first and second sets of fixing elements 102, 104, as shown in FIG. 2. As shown, the second spinal rod 113 extends substantially parallel to the first spinal rod 112. The first and second spinal rods 112, 113 are used to maintain the realignment of the spinal column 101 after surgery.

The linkage 148 can have a variety of configurations. For example, as shown in more detail in FIG. 7, the linkage 148 includes first and second linking arms 150, 152, each having a primary arm 150a, 152a and a secondary arm 150b, 152b. In this illustrated embodiment, the linking arms 150, 152 are structurally identical, whereas in other embodiments, the linking arms 150, 152 can be structurally different.

Figure 7:
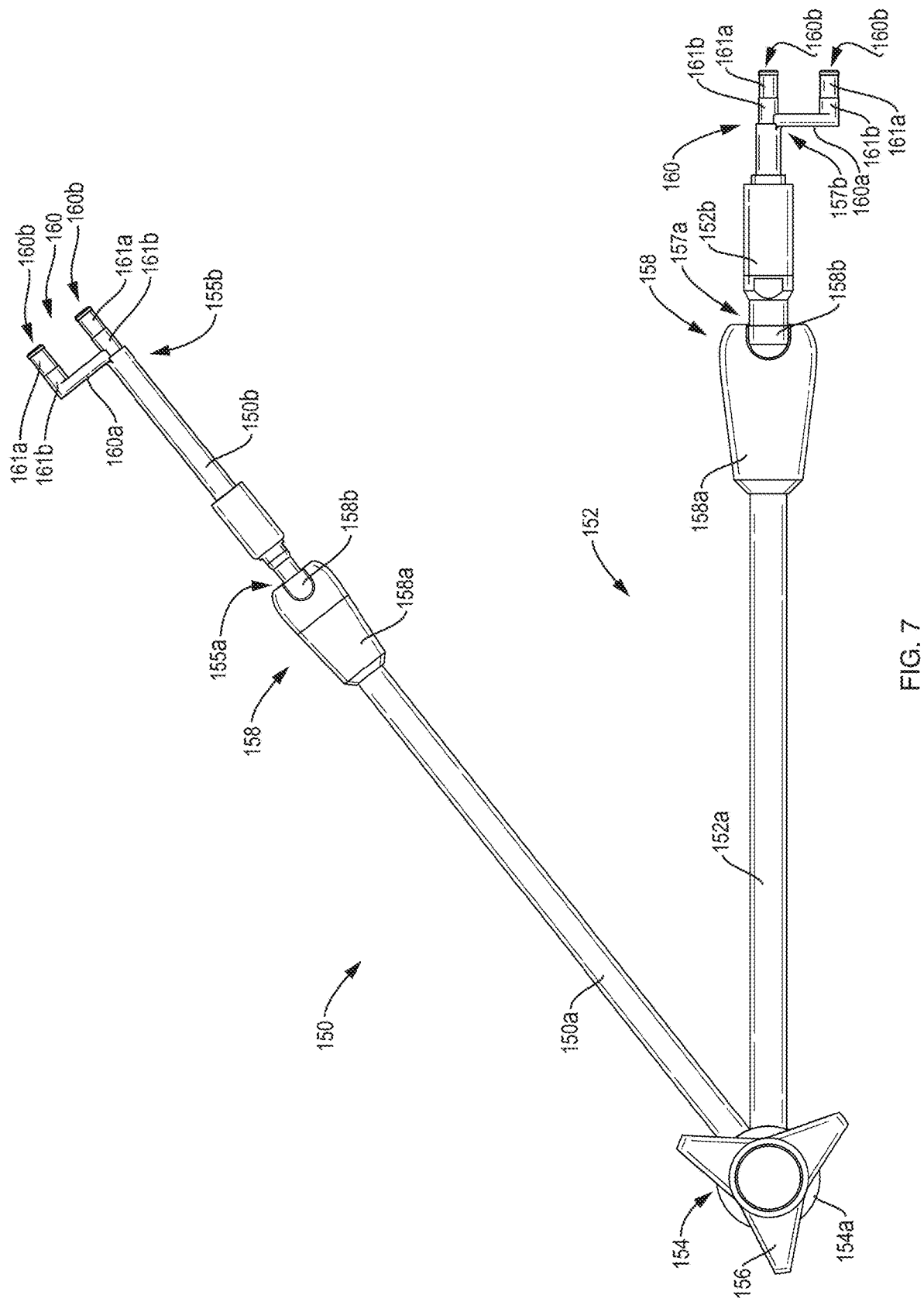
FIG. 7 is a front view of the linkage of FIG. 6.

The first and second linking arms 150, 152 are pivotally coupled together at a joint assembly 154. The joint assembly 154 can have a variety of configurations. For example, in some embodiments, as shown in FIG. 7, the joint assembly 154 includes two segments 154a, 154b that are operable engaged with each other via a pivot pin (not shown). Each segment can have variety of configurations. For example, each illustrated segment 154a, 154b has a substantially cylindrical configuration. Further, the first and second segments 154a, 154b are coupled to the first ends 151a, 151b of the primary arms 150a, 152a of the first and second linking arms 150, 152, respectively. While not shown, the pivot pin extends through a first channel of the first segment 154a and engages (e.g., a threaded engagement) with a second channel of the second segment 154b. As discussed in more detail below, the joint assembly 154 has an unlocked configuration that allows the first and second linking arms 150, 152 to be angularly adjusted relative to each other and a locked configuration that prevents the first and second linking arms 150, 152 from moving relative to each other, thereby locking the arms 150, 152 in a desired angular orientation.

As further shown in FIG. 7, a locking element 156 is coupled to an end of the pivot pin such that rotation of the locking element 156 in a first direction (e.g., a clockwise direction) locks the joint assembly 154, and therefore maintains the first and second linking arms 150, 152 in a first orientation (e.g., angular orientation) relative to one another. For example, in use, rotating the locking element 156 in the first direction causes the first and second segments 154a, 154b of the joint assembly 154 to be urged towards each other, thereby creating an interference or friction fit therebetween. This friction fit immobilizes the two segments 154a, 154b, and therefore locks the joint assembly 154. To unlock the joint assembly 154, a user rotates the locking element 156 in a second direction (e.g., counter clockwise), releasing the pressure induced on the two segments 154a, 154b. In this illustrated embodiment, the locking element 156 is a three-lobe knob. In other embodiments, the locking element 156 can have other configurations, e.g., a t-shaped configuration. It should be noted that other locking configurations and mechanisms can be used.

As noted above, each linking arm 150, 152 also includes a secondary arm 150b, 152b that can be pivotally coupled to its respective primary arm 150a, 152a. While any suitable pivot configuration can be used, the two secondary arms 150b, 152b can be movable relative to their respective primary arms 150a, 152a by using a ball and socket joint 158, as illustrated. That is, the second end 153b, 153b of each primary arm 150a, 152b can include a socket 158a with an interior mating surface that seats a ball-shaped element 158b at a first end 155a, 157a of its corresponding secondary arm 150b, 152b. It should be noted that the sockets 158a and the ball-shaped elements 158b can have other shapes that facilitate similar pivoting configurations, including, for example, spherical (as illustrated), toroidal, conical, frusto-conical, and any combinations of these shapes. Further, the joint assembly 154 can also be operably coupled to the ball and socket joints 158 such that placement of joint assembly 154 in a locked configuration also locks the ball and socket joints 158. For example, actuation of the locking element 156 can cause inner shafts (not shown) disposed within each primary arm 150a, 152a to translate longitudinally into engagement with the ball-shaped elements 158b, applying a frictional force thereto to resist or prevent movement of the ball and socket joint 158. As a result, the joint assembly 154 and the ball and socket joints 158 can be locked and unlocked substantially simultaneously by rotation of the locking element 156 in the first and second directions, respectively.

Further, as shown in FIG. 7, a second end 155b, 157b of each secondary arm 150b, 152b includes a connector 160. These connectors 160 are configured to couple the linkage 148 to the first and second frames 118, 120, as shown in FIGS. 1 and 7. While the connectors 160 at the second ends 155b, 157b can have a variety of configurations, the connectors 160, which are shown in detail in FIG. 7, each include a base 160a with two opposing legs 160b extending outwardly therefrom. As shown in FIGS. 1 and 6, the two opposing legs 160b of the first secondary arm 150b are inserted into two mating features of the set of mating features 134 of the first frame 118, and the opposing legs 160b of the second secondary arm 152b are inserted into two mating features of the set of mating features 134 of the second frame 120. Connecting the linkage 148 to each frame 118, 120 at two discrete connection points (e.g., at first and second legs 160b as shown) can provide a sturdier construct that resists or prevents unintended "racking" type movement, e.g., in which the linkage 148 inadvertently rotates relative to the frame at the connection point.

While the legs 160b of the connectors 160 can have a variety of shapes, the legs 160b shown in FIG. 7 are in the form of substantially cylindrical pins. Further, the legs 160b each have a substantially constant diameter along a first portion 161a thereof and an enlarged outer diameter along a second portion thereof 161b. Since the first portion 161a of the legs 160b are inserted in the mating features first, the varying diameter can allow for easier insertion, while also allowing for a tighter fit between the legs and respective mating features once the legs 160b are completely inserted therein. In other embodiments, the legs 160b can each have a substantially constant outer diameter along their entire length.

Figure 8:
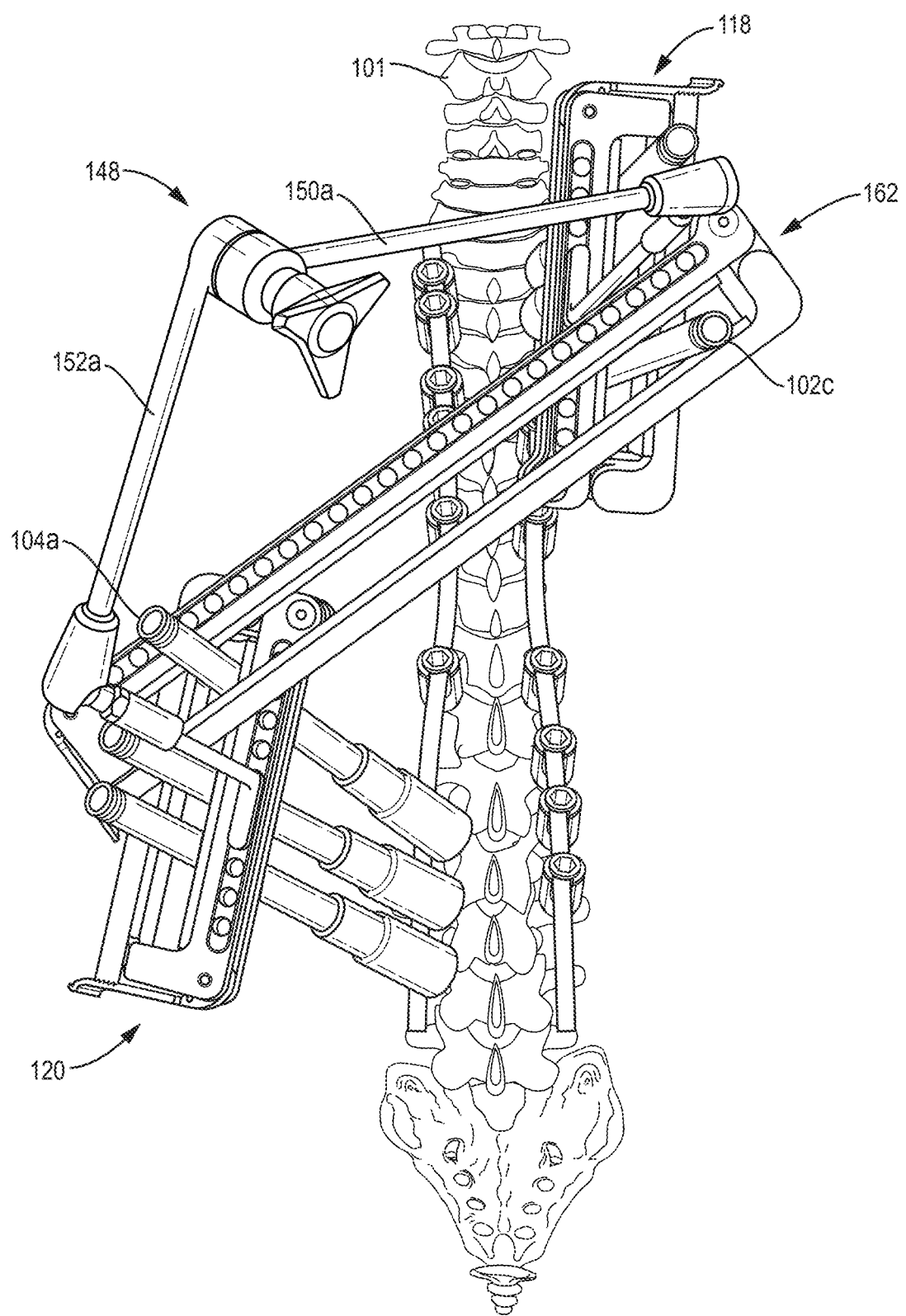
FIG. 8 is perspective view of the system of FIG. 1 showing a third frame clamped to one fixing element of the first set of fixing elements and one fixing element of the second set of fixing elements.

In some embodiments, additional frames can be used to further assist in maintaining a correction of the spinal column 101. For example, as shown in FIG. 8, a third frame 162 is used to clamp one fixing element 102c of the first set of fixing elements 102 to one fixing element 104a of the second set of fixing elements 104. As a result, the third frame 162 can offer additional stabilization to the derotated spinal column during surgery. While the illustrated arrangement includes both a third frame 162 and a linkage 148, in other arrangements the linkage 148 can be omitted.

Figure 9:
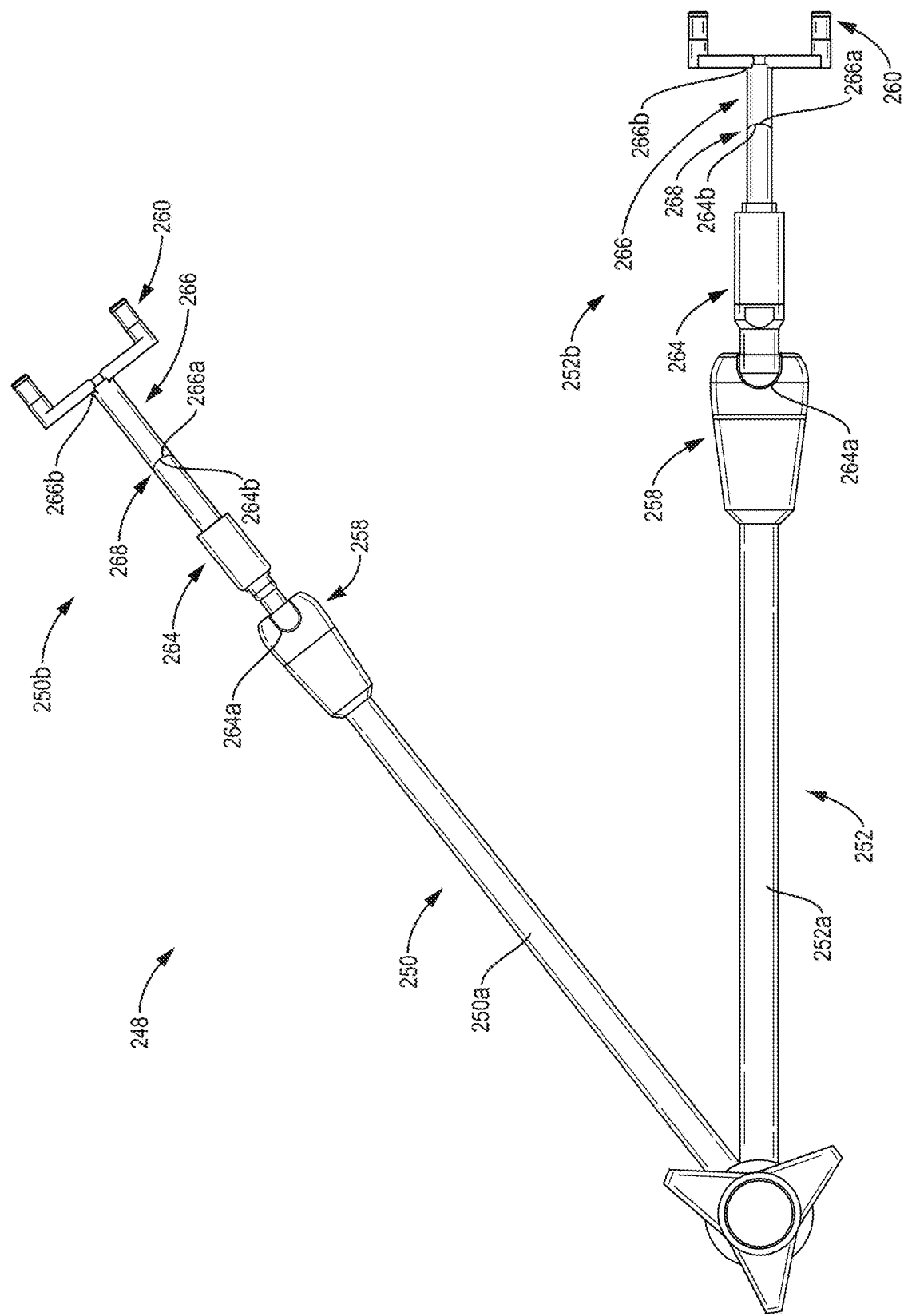
FIG. 9 is a front view of another embodiment of a linkage having first and second linking arms.

In some embodiments, the secondary arms can be configured in such a way that an additional joint can be formed within the linkage. FIG. 9 illustrates another exemplary embodiment of a linkage 248, which is similar to linkage 148 in FIGS. 1 and 6-7, except for the differences described below.

As shown, the linkage 248 includes first and second linkage arms 250, 252 each having a primary arm 250a, 252a and a secondary arm 250b, 252b. In this illustrated embodiment, the secondary arms 252b each include first and second segments 264, 266. The first and second segments 264, 266 each extend from a first end 264a, 264a to a second end 266a, 266a. As shown, the first end 264a, 264b of first segments are coupled their respective primary arm 250a, 252a using a ball and socket joint 258, like ball and socket joint 158 in FIGS. 1 and 6-7. Further, a connector 260 is coupled to each second end 264b, 266b of each second segment 264, 266. For sake of simplicity, the following description is with respect to the secondary arm 250b of the first linking arm 250. A person skilled in the art will understand, however, that the following discussion is also applicable to the secondary arm 252b of the second linking arm 252, which as shown in FIG. 9 is structurally similar to that of the secondary arm 250b.

As shown, the first and second segments 264, 266 of the secondary arm 250b are pivotally connected to each other at a selectively locked joint 268. The joint 268, as shown in FIG. 9, is formed between the second end 264b of the first segment 264 and the first end 266a of the second segment 266. The second end 264b of the first segment 264 has a convex surface that engages with a concave surface of the first end 266a of the second segment 266. When the convex and concave surfaces are fully engaged, as shown in FIG. 9, a friction fit is created therebetween. This friction fit locks the joint 268 such that the first and second segments 264, 266 remain fixed relative to each other. As shown, when the joint 268 is locked, the first and second segments 264, 266 are in a substantially straight configuration. It should be noted in other embodiments, the first and second segments 264, 266 can have other types of configurations when the joint 268 is locked.

To unlock the joint 268, a user applies a sufficient amount of force to the second segment 266 to overcome the frictional forces at the interface of the convex and concave surfaces. As a result, the second segment 266 can then move (e.g., bend) relative to the first segment 264 about the joint 268. That is, the second segment 266 can be manipulated to help position and insert the connector 260 into a receiver of a frame, like one of the receivers 134 of first frame 118 in FIGS. 1 and 3-6.

Figure 10:
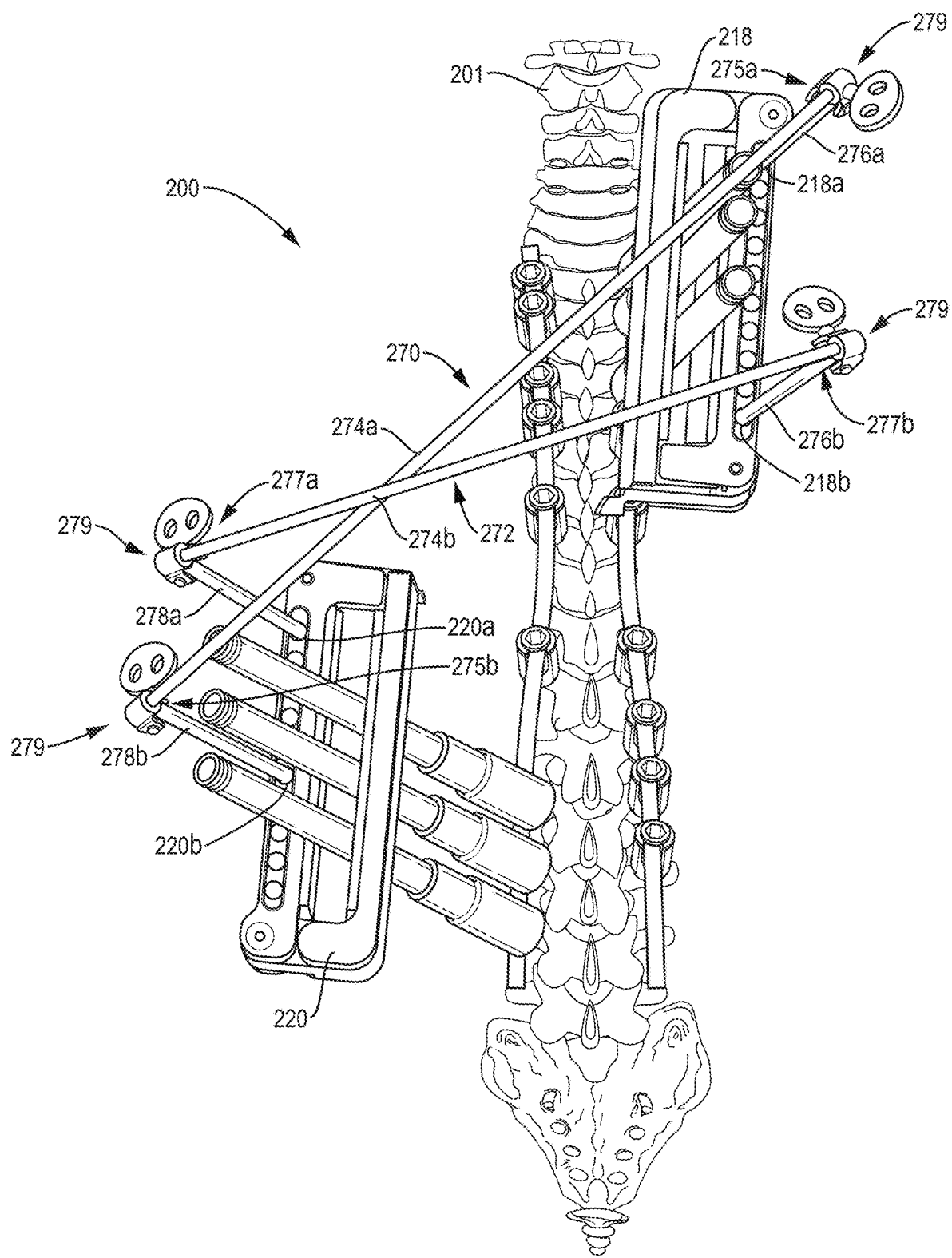
FIG. 10 is a perspective view an embodiment of a system that includes two linkages, with each linkage having a linking arm coupled to two connectors that are coupled to first and second frames, respectively.

FIG. 10 illustrates another exemplary system used in an en bloc derotation method. As shown, the system 200 is engaged with a spinal column 201. Aside from the differences discussed below, the system in FIG. 10 is similar to the system 100 in FIGS. 1-6-7. Further, the system 200 is illustrated after the spinal column 201 has been derotated. The system 200 includes first and second linkages 270, 272 that each couple a first frame 218, like first frame 118 in FIGS. 1 and 3-6, to a second frame 220, like second frame 120 in FIGS. 1 and 3-6. Each linkage 270, 272 includes a linking arm 274a, 274b and first and second connectors 276a, 276b, 278a, 278b that are coupled to opposing ends 275a, 275b, 277a, 277b of respective linking arms 274a, 274b. While the first and second connectors 276a, 276b, 278a, 278b can be coupled to the linking arm 274a, 275b using a variety of coupling mechanisms, in the embodiment shown in FIG. 10, the coupling mechanism is in the form of a c-clamp assembly 279. As shown, the first and second connectors 276a, 276b, 278a, 278b of each linkage 270, 272 is respectively coupled to the first frame 218 and the second frame 220. More specifically, the first connectors 276a, 276b are inserted into first receivers 218a, 218b of the first frame 218 and the second connectors 278a, 278b are inserted into second receivers 220a, 220b of the second frame 220. As a result, the first and second frames 218, 220 are maintained in a fixed position relative to each other, thereby maintaining the spinal column 201 in the derotated configuration.

Figure 11:
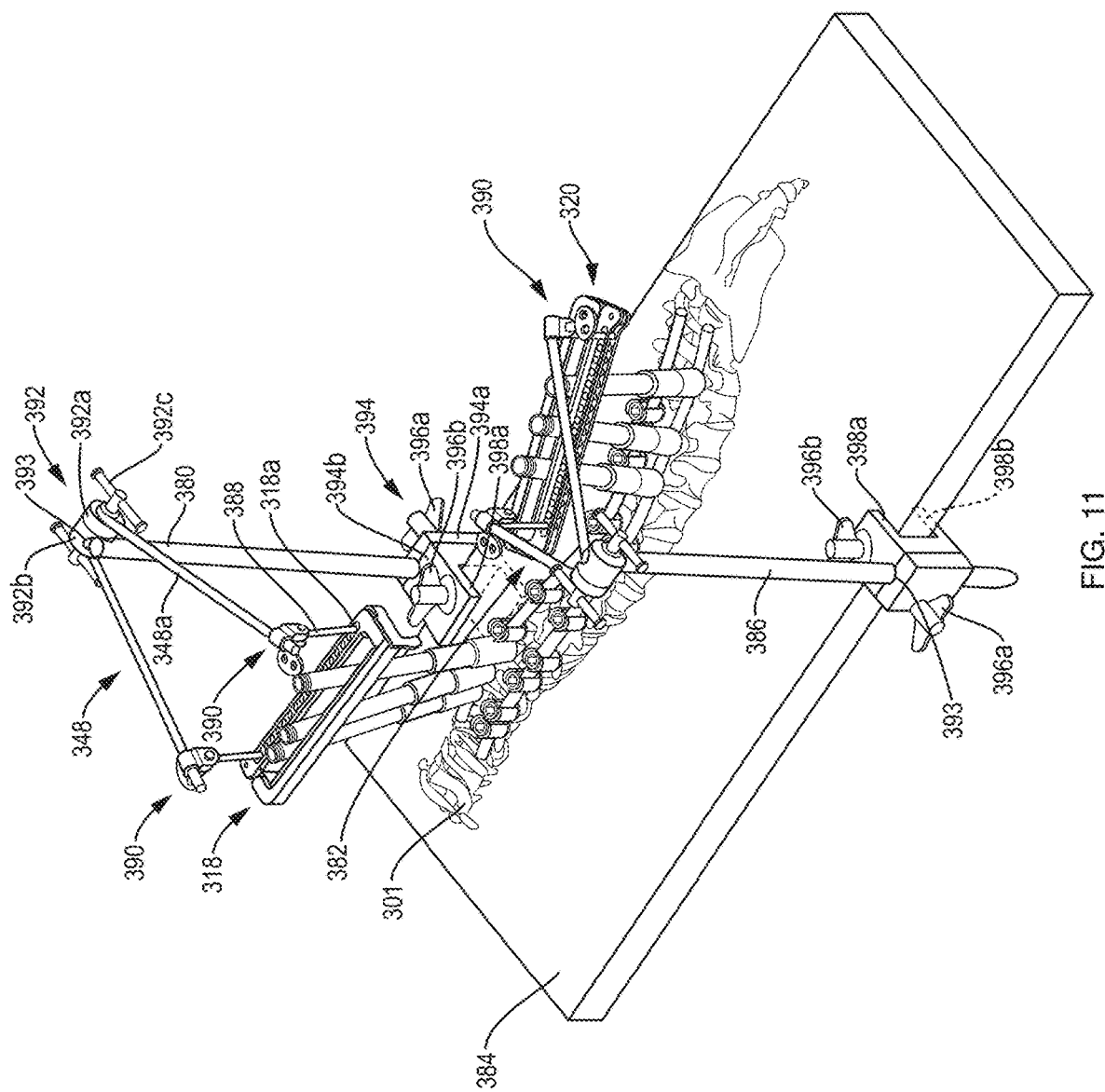
FIG. 11 is a perspective view of an embodiment of a system that includes another embodiment of a linkage coupled respectively to first and second frames and to a stationary support.

In other embodiments, after derotation, linkages can be used to couple first and second frames to a stationary item, such as an operating table, to maintain the spinal column in a derotated configuration. For example, as shown in FIG. 11, a first linkage 348 is used to fixedly couple a first frame 318, which is similar to first frame 118 in FIGS. 1 and 2-6, to a first support member 380 that is fixedly coupled to an operating table 384, and a second linkage 382 is used to fixedly couple a second frame 320, which is similar to second frame 120 in FIGS. 1-3 and 5-6, to a second support member 386 that is also fixedly coupled to the operating table 384. For sake of simplicity, the following description is with respect to the first linkage 348. A person skilled in the art will understand, however, that the following discussion is also applicable to the second linkage 382, which as shown in FIG. 11 is structurally similar to that of the first linkage 348.

As shown, the first linkage 348 includes a linking arm 348a that is coupled between a first connector 388 and the first support member 380. The first connector 388 is fixedly coupled to the linking arm 348a using a first clamping assembly 390. While the first clamping assembly 390 can have a variety of the configuration, the first clamping assembly 390, as shown in FIG. 11 is in the form of a c-clamp. After the spinal column 301 has been derotated, as shown in FIG. 11, the first connector 388 is inserted into a receiver 318a of the first frame 318 and the linking arm 348a is then coupled to the first connector 388.

As further shown, the first support member 380 is fixedly coupled to the linking arm 348a using a second clamping assembly 392. While the second clamping assembly 392 can have a variety of configurations, the second clamping assembly 392, as shown in FIG. 11, includes two segments 392a, 392b that are operably coupled to each other. Further, the second segment 392b has a cut-out portion 393 that is configured to receive and abut against a portion the first support member 380. The second clamping assembly 392 also includes a locking mechanism having a locking element 392c that is threadably engaged with the first and second segments 392a, 392b. As such, rotating the locking element 392c in a first direction (e.g., clockwise) urges the first and second segments 392a 392b together while also causing the first support member 380 to engage with the cut-out portion 393 of the second segment 392b. To unlock the second clamping assembly, a user rotates the locking element in a second direction (e.g., counter clockwise). Thus, once the linking arm 348a is coupled to the first connector 388, the linking arm 348a can be fixedly coupled to the first support member 380 by rotating the locking element 392c in the first direction. While the locking element can have a variety of configuration, the locking element 382c, as shown in FIG. 11, has a t-shaped configuration.

Further, a third clamping assembly 394 is used to fixedly clamp the first support member 380 to the operating table 384. While the third clamping assembly can have a variety of configurations, the third clamping assembly, as shown in FIG. 11, includes two segments 394a, 394b that are operably engaged with each other in which the first segment 394a is selectively coupled to the first support member 380 by a first locking element 396a and the second segment 394b is selectively coupled to the operating table 384 by a second locking element 396b. The first locking element 396a is configured to selectively rotate so as to urge the first and second segments 394a, 394b together such that the first support member 380 is secured therebetween, as shown in FIG. 11. The second locking element 396b is configured to selectively rotate causing two arms 398a, 398b extending from the second segment 394b to engage with and secure to a portion of the operating table 384 positioned therebetween, as shown in FIG. 11.

In any of the foregoing embodiments, once a linkage assembly is locked, a surgeon can perform additional maneuvers (such as well-known compression, distraction, contouring techniques, and the like). For example, a surgeon can either apply a compression force or distraction force to fixture elements of the first or second sets of fixture elements to cause respective vertebra coupled thereto to move toward or away from each other using any suitable known techniques. Alternatively or in addition, a surgeon can tighten the closure mechanisms of the bone anchors using any suitable known technique. For example, in one embodiment, a surgeon can insert a driving instrument into each fixing element of the first and second plurality of fixing elements to tightening the closing element of the respective bone anchors coupled thereto. Once secured and final-tightened to the bone anchors, the spinal rods or other fixation elements maintain correction of the spine and any of the fixing elements, frames, and linkages can be removed and the surgical incision closed using known techniques.

Additional embodiments are also provided as follows:

Clause 1. A surgical method for en bloc derotating a spinal column, the method comprising:
coupling a first clamp to a first screw extension coupled to a first vertebra;
coupling a second clamp to a second screw extension coupled to a second vertebra;
rotating the first and second clamps relative to one another to derotate the first vertebra and the second vertebra relative to one another; and
coupling a linkage to the first and second clamps and locking the linkage to maintain the first and second clamps in a fixed position relative to one another, thereby maintaining the first vertebra and the second vertebra in a derotated position relative to one another.

Clause 2. The method of clause 1, wherein coupling the first clamp to the first screw extension coupled to the first vertebra further comprises coupling the first clamp to a third screw extension coupled to a third vertebra, and coupling the second clamp to the second screw extension coupled to the second vertebra further comprises coupling the second clamp to a fourth screw extension coupled to a fourth vertebra.

Clause 3. The method of clause 1, wherein the first vertebra is located in the lumbar spine and the second vertebra is located in the thoracic spine.

Clause 4. The method of clause 1, wherein locking the linkage comprises rotating a locking element on the linkage to lock first and second arms of the linkage in a fixed angular orientation relative to one another.

Clause 5. The method of clause 1, further comprising coupling the linkage to a support member mounted on an operating table.

Clause 6. The method of clause 1, wherein coupling the linkage to the first and second clamps comprises inserting a first connector at a first end of the linkage into a first receiving member of the first clamp, and inserting a second connector at a second end of the linkage into a second receiving member of the second clamp.

Clause 7. The method of clause 6, wherein the first and second connectors each include a pair of legs and the first and second receiving members each include a pair of bores that receives the legs when the first and second connectors are coupled to the first and second receiving members.

Clause 8. The method of clause 1, further comprising, prior to coupling the first and second clamps, driving a first bone anchor into the first vertebra to couple the first screw extension to the first vertebra, and driving a second bone anchor into the second vertebra to couple the second screw extension to the second vertebra.

Clause 9. A surgical method for en bloc derotating a spinal column, the method comprising:
manipulating first and second clamps coupled respectively to a first plurality of vertebrae and a second plurality of vertebrae to derotate the first and second plurality of vertebrae relative to one another; and
subsequently locking first and second arms of a linkage assembly coupled respectively to the first and second clamps to maintain the first and second arms in a first angular orientation relative to one another, thereby maintaining the clamps in a fixed position and maintaining the first and second plurality of vertebrae in a derotated position.

Clause 10. The method of clause 9, further comprising, prior to locking, non-rotatably coupling the first arm of the linkage assembly to the first clamp and non-rotatably coupling the second arm of the second linkage assembly to the second clamp.

Clause 11. The method of clause 9, wherein the first plurality of vertebrae are located in the lumbar spine and the second plurality of vertebrae are located in the thoracic spine.

Clause 12. The method of clause 9, wherein locking the linkage comprises rotating a locking element on the linkage.

Clause 13. The method of clause 9, further comprising coupling the linkage to a support member mounted on an operating table.

Clause 14. A surgical method for en bloc derotating a spinal column, the method comprising:

clamping a first frame to a first plurality of fixture elements coupled to a first plurality of vertebrae;

clamping a second frame to a second plurality of fixture elements coupled to a second plurality of vertebrae that differs from the first plurality of vertebrae;

rotating the first plurality of fixture elements and the second plurality of fixture elements relative to each other, thereby manipulating at least a portion of the spinal column into a derotated configuration;

attaching a first end of a first arm of a linkage assembly to the first frame and a second end of a second arm of the linkage assembly to the second frame so as to bridge the first plurality of fixing elements to the second plurality of fixing elements; and locking the first and second arms of the linkage assembly relative to one another to lock the first plurality of fixture elements and the second plurality of fixing elements in a fixed position relative to each other such that the spinal column is maintained in the derotated configuration.

Clause 15. The method of clause 14, wherein the first plurality of vertebrae are located in the lumbar spine and the second plurality of vertebrae are located in the thoracic spine.

Clause 16. The method of clause 14, further comprising coupling the linkage assembly to a support member mounted on an operating table.

Clause 17. The method of clause 14, wherein attaching the first end of the first arm to the first frame comprises inserting first and second male members into first and second receivers in the first frame, and attaching the second end of the second arm to the second frame comprises inserting third and fourth male members into third and fourth second receivers in the second frame.

Clause 18. The method of clause 14, further comprising applying a compression force to first and second fixture elements of the first plurality of fixture elements to cause respective vertebra coupled thereto to move towards each other.

Clause 19. The method of clause 14, further comprising applying a distraction force to first and second fixture elements of the first plurality of fixture elements to cause respective vertebra coupled thereto to move away from each other.

Clause 20. The method of clause 14, further comprising, prior to clamping the first and second frames, driving a bone anchor coupled to each of the first and second plurality of fixture elements into the first and second plurality of vertebrae to couple the first and second plurality of fixture elements to the first and second plurality of vertebrae.

The systems and devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claim is:

1. A system for en bloc derotation of a spinal column, comprising:

a first frame configured to couple to a first plurality of fixing elements attached to a first plurality of vertebrae;

a second frame configured to couple to a second plurality of fixing elements attached to a second plurality of vertebrae distinct from the first plurality of vertebrae and derotated relative to the first plurality of vertebrae;

first and second arms respectively coupled to the first and second frames, the first and second arms being hingedly coupled to each other via a pivot pin such that the first and second arms are configured to pivot about the pivot pin, the first and second arms comprising respective first and second primary arms and respective first and second secondary arms; and a locking mechanism coupled to the end of the pivot pin, wherein actuation of the locking mechanism is configured to fix an angular orientation between the first and second arms to maintain derotation between the first plurality of vertebrae and the second plurality of vertebrae, wherein the first frame and the second frame each comprise a plurality of bores configured to receive complimentary mating features of the first and second arms; and wherein the first and second secondary arms each comprise a plurality of extensions configured to extend through the plurality of bores.

2. The system of claim 1, wherein the first and second primary arms are respectively coupled to the first and second secondary arms via ball and socket joints.

3. The system of claim 1, wherein the first frame and the second frame each comprise:
a first arm member; and
a second arm member pivotally coupled to the first arm member, the second arm member being pivotable relative to the first arm member between an open position and a closed position,
wherein a rectangular slot configured to receive a plurality of fixing elements is defined between the first arm member and the second arm member in the closed position.

4. The system of claim 3, wherein the first frame and the second frame each comprise a locking arm coupled to the first arm member and configured to lock the second arm member to the first arm member in the closed position.

5. The system of claim 3, wherein at least one of the first arm member and the second arm member includes a pad extending into the rectangular slot.

6. A system for en bloc derotation of a spinal column, comprising:
a first plurality of fixing elements configured to couple to a first plurality of vertebrae;
a second plurality of fixing elements configured to couple to a second plurality of vertebrae distinct from the first plurality of vertebrae;
a first frame coupled to the first plurality of fixing elements;
a second frame coupled to the second plurality of fixing elements
a third frame coupled to a fixing element in the first plurality of fixing elements and a fixing element in the second plurality of fixing elements; and
a linkage coupled to the first frame and the second frame, comprising:
a first arm coupled to the first frame;
a second arm coupled to the second frame and hingedly coupled to the first arm via a pivot pin such that the first and second arms are configured to pivot relative to each other about the pivot pin; and
a locking mechanism configured to be actuated to cause the first arm and the second arm to engage each other to fix an angular orientation between the first arm and the second arm to maintain derotation between the first plurality of vertebrae and the second plurality of vertebrae.

7. The system of claim 6, wherein the first frame and the second frame each comprise:
a first arm member; and
a second arm member pivotally coupled to the first arm member, the second arm member being pivotable relative to the first arm member between an open position and a closed position,
wherein a rectangular slot configured to receive a plurality of fixing elements is defined between the first arm member and the second arm member in the closed position.

8. The system of claim 7, wherein the first frame and the second frame each comprise a locking arm coupled to the first arm member and configured to lock the second arm member to the first arm member in the closed position.

9. The system of claim 7, wherein at least one of the first arm member and the second arm member includes a pad extending into the rectangular slot.

10. The system of claim 7, wherein the plurality of fixing elements are linearly aligned when received in the rectangular slot.

11. The system of claim 6, wherein the first frame and the second frame each comprise a plurality of bores, the plurality of bores being configured to receive complimentary mating features of the first and second arms.

12. The system of claim 11, wherein the first arm comprises a first primary arm and a first secondary arm and the second arm comprises a second primary arm and a second secondary arm, and wherein the first secondary arm and the second secondary arm each comprise a plurality of extensions configured to extend through the plurality of bores.

* * * * *